(12) United States Patent
Fischer

(10) Patent No.: US 9,119,580 B2
(45) Date of Patent: Sep. 1, 2015

(54) DETECTION DEVICE FOR DETECTION A BLOOD PICTURE PARAMETER

(75) Inventor: Georg Fischer, Nuremberg (DE)

(73) Assignees: eesy-id GmbH, Grafelfing (DE); Friedrich-Alexander-Universitaet Erlangen-Nuernberg, Erlangen (DE)

(*) Notice: Subject to any disclaimer, the term of this patent is extended or adjusted under 35 U.S.C. 154(b) by 61 days.

(21) Appl. No.: 13/884,347

(22) PCT Filed: Oct. 28, 2011

(86) PCT No.: PCT/EP2011/069029
§ 371 (c)(1),
(2), (4) Date: Jul. 17, 2013

(87) PCT Pub. No.: WO2012/069280
PCT Pub. Date: May 31, 2012

(65) Prior Publication Data
US 2013/0303866 A1    Nov. 14, 2013

(30) Foreign Application Priority Data

Nov. 24, 2010  (EP) .................................... 10192470

(51) Int. Cl.
*A61B 5/1455* (2006.01)
*A61B 5/145* (2006.01)
*A61B 5/05* (2006.01)
*A61B 5/00* (2006.01)

(52) U.S. Cl.
CPC ........... *A61B 5/14532* (2013.01); *A61B 5/0004* (2013.01); *A61B 5/0507* (2013.01); *A61B 5/14542* (2013.01); *A61B 5/14546* (2013.01); *A61B 5/6824* (2013.01); *A61B 5/7225* (2013.01)

(58) Field of Classification Search
CPC ....................................................... A61B 12/006
USPC .................................................. 600/310–344
See application file for complete search history.

(56) References Cited

U.S. PATENT DOCUMENTS

| | | | |
|---|---|---|---|
| 2005/0085725 | A1 | 4/2005 | Nagar et al. |
| 2006/0025664 | A1 | 2/2006 | Kim et al. |
| 2009/0275814 | A1 | 11/2009 | Watanabe et al. |

FOREIGN PATENT DOCUMENTS

| | | |
|---|---|---|
| GB | 2428093 A | 1/2007 |
| WO | WO-2010131029 A1 | 11/2010 |

OTHER PUBLICATIONS

International Search Report for PCT/EP2011/069029 dated Feb. 17, 2012.

*Primary Examiner* — Eric Winakur
*Assistant Examiner* — Marjan Fardanesh
(74) *Attorney, Agent, or Firm* — Marshall, Gerstein & Borun LLP

(57) ABSTRACT

A detection device for detecting a blood count parameter in a blood vessel, comprising a transmitter to inject a first transmit signal of a first frequency into the blood vessel and a second transmit signal of a second frequency into the blood vessel, a receiver to receive a first receive signal at the first frequency and a second receive signal at the second frequency, a loss detector to determine a first loss value on the basis of the first transmit signal and the first receive signal at the first frequency, and to determine a second loss value on the basis of the second transmit signal and the second receive signal at the second frequency, and a processor to determine a first frequency shift of the first loss value relative to a first reference loss value, determine a second frequency shift of the second loss value relative to a second reference loss value, and determine the blood count parameter on the basis of the first frequency shift and the second frequency shift.

20 Claims, 19 Drawing Sheets

| Diam. El | A | B | C | D | E | F | G |
|---|---|---|---|---|---|---|---|
| 6 mm | <1 | +2 | -1 | -9 | -17 | +11 | <1 |
| 4 mm | -1 | +4 | -1 | -13 | - | - | -10 |

DETECTION DEVICE FOR DETECTION A BLOOD PICTURE PARAMETER

BACKGROUND OF THE INVENTION

1. Field of the Invention

The present invention relates to the field of detecting a concentration of a blood constituent, for example a concentration of blood sugar.

2. Related Technology

In order to ascertain a blood picture parameter, such as, for example, a concentration of a blood constituent, blood can be taken invasively. The blood picture parameter can then be ascertained using the taken blood by means of standardized test strips, the electric resistance values of which depend on the concentration of the blood constituent, e.g. blood sugar. By way of example, the respective electric resistance value can be detected using a blood sugar measuring instrument, which carries out a DC current resistance measurement for detecting an electric resistance value of a test strip. The resistance value can be converted into a blood sugar concentration on the basis of a relationship, known per se, between a blood sugar concentration and a resistance value. In order to obtain high detection accuracy, each test strip is provided with calibration data, for example with a reference resistance value or with a corresponding code, as a result of which variations of properties of the test strips can be compensated for. However, a disadvantage of invasive methods is the necessity of taking blood and hence of injuring a patient. Moreover, continuous detection of a concentration of a blood constituent, for example to establish the diurnal variation curve thereof, is complicated. Furthermore, it is not possible to detect a time delay between food being taken and, for example, an increase in the blood sugar accurately by means of the invasive method. Also, particularly in the case of a low concentration of the blood sugar in blood, the time for administering insulin to the patient cannot be ascertained accurately.

For noninvasive ascertaining of a blood picture parameter such as, for example, a substance concentration or a substance composition in the blood, use can be made of microwave-spectroscopic methods. Microwave spectroscopy for detecting blood picture parameters is based on coupling a microwave signal into tissue perfused by blood and detecting a frequency-dependent absorption of coupled-in microwave energy.

The article "Non-invasive glucose monitoring in patients with Type 1 diabetes: A multi-sensor system combining sensors for dielectric and optical characterization of skin", Biosensors and Bioelectronics 24 (2009) 2778-2784 by Andreas Caduff et al. describes a multi-electrode arrangement for microwave-based ascertaining of a blood picture parameter. The multi-electrode arrangement comprises a plurality of electrode pairs with different electrode spacings, by means of which different penetration depths of microwave signals can be realized. The blood picture parameter is detected by means of an impedance measurement, i.e. by means of a one-port measurement, and is therefore susceptible to errors in the case of possible impedance maladjustments. As a result of different penetration depths, it is sometimes not possible to distinguish between capillary and venous blood, which can falsify the measurement results. In general, a measurement of a blood picture parameter using venous blood is more precise than a measurement of the blood picture parameter using capillary blood because, for example, blood sugar changes in capillary blood are delayed compared to venous blood.

The articles "A microwave frequency sensor for non-invasive blood-glucose measurement", SAS 2008—IEEE Sensors Applications Symposium, Atlanta, Ga., Feb. 12-14, 2008, by Buford Randal Jean et al. and "Calibration methodology for a microwave non-invasive glucose sensor", Master's Thesis, Baylor University, May 2008 by M. McClung describe a further electrode arrangement for ascertaining a blood sugar concentration. What is exploited here is that the dielectric properties of blood depend on a blood sugar content. By pressing a thumb onto the microwave sensor, a change in the relative permittivity of the thumb is measured by a detuning of a resonator. However, blood is displaced by the contact pressure of the thumb, and this can lead to falsification of the measurement results. Moreover, the measurements cannot be carried out continuously. The evaluation of the measurement data for ascertaining the blood sugar content moreover depends on the respective patient and is therefore not reproducible in other patients. Moreover, this method does not allow control of the penetration depth of the microwave power, and so it is not possible to distinguish between capillary and venous blood. Furthermore, the change in the relative permittivity is carried out on the basis of a one-port measurement, which is susceptible in respect of maladjustments.

SUMMARY OF THE INVENTION

The invention provides an efficient concept for microwave-based, non-invasive ascertaining of a blood picture parameter, in particular of a concentration of blood sugar, in blood flowing through a blood vessel.

Accordingly, the invention provides a detention device for detecting a blood picture parameter of blood vessel, comprising:

a transmitter, which is configured to couple a first transmission signal with a first frequency and a second transmission signal with a second frequency into the blood vessel;

a receiver, which is configured to receive a first reception signal at the first frequency and a second reception signal at the second frequency; and a loss detector, which is configured to:

ascertain a first loss variable on the basis of the first transmission signal and the first reception signal at the first frequency; and ascertain a second loss variable on the basis of the second transmission signal and the second reception signal at the second frequency; and a processor, which is configured to:

ascertain a first frequency shift of the first loss variable relative to a first reference loss variable; ascertain a second frequency shift of the second loss variable relative to a second reference loss variable; and ascertain the blood picture parameter on the basis of the first frequency shift and the second frequency shift.

The invention further provides a method for detecting a blood picture parameter of blood in a blood vessel, comprising the step of:

coupling a first transmission signal with a first frequency into the blood vessel;

coupling a second transmission signal with a second frequency into the blood vessel;

receiving a first reception signal at the first frequency;

receiving a second reception signal at the second frequency;

establishing a first loss variable on the basis of the first transmission signal and the first reception signal at the first frequency;

establishing a second loss variable on the basis of the second transmission signal and the second reception signal at the second frequency;

ascertaining a first frequency shift of the first loss variable relative to a first reference loss variable;

ascertaining a second frequency shift of the second loss variable relative to a second reference loss variable; and ascertaining the blood picture parameter on the basis of the first frequency shift and of the second frequency shift.

The invention is based on the discovery that a blood picture parameter can be ascertained by detecting a frequency shift of one or more absorption lines of a blood constituent. By way of example, if the blood picture parameter to be ascertained is a concentration of blood sugar in the blood, a frequency shift of absorption lines of a water solution containing sugar is a measure for the concentration of the blood sugar, i.e. for the blood sugar level. By observing a frequency shift at a number of absorption lines, the reliability of ascertaining the blood parameter can moreover be increased further. Detecting the blood picture parameter on the basis of the frequency shift of the absorption lines is based on the further discovery that the viscosity of a water solution may change with increasing sugar concentration, as a result of which, for example, the absorption lines of a water/sugar solution can occur at lower frequencies than absorption lines of pure water. This is how it is possible to detect the concentration of the blood sugar by detecting a frequency shift of one or more absorption lines in a frequency range of, for example, 2 to 12 GHz.

The invention is based on the further discovery that a blood vessel such as, for example, a vein or an artery, the fatty tissue surrounding this blood vessel and the layer of skin situated thereover can be considered to be a dielectric waveguide system. Thus, if such a dielectric waveguide system is excited, it is possible to excite different modes or waves types, for example a transverse electromagnetic (TEM) wave or transverse electric (TE) wave or transverse magnetic (TM) wave or an HE wave. In the case of a TE wave, there is a component of the magnetic field, different from zero, which points in the propagation direction. By contrast, in the case of a TM wave, there is a component of an electric field, different from zero, which points in the mode propagation direction. Thus, depending on a radiofrequency excitation, it is possible to excite different modes in a dielectric waveguide system, which comprises the blood vessel and the layer of skin, which modes can also propagate in the blood flow direction, as a result of which an accurate detection of a blood picture parameter is possible.

In accordance with one aspect, the invention relates to a detection device for detecting a blood picture parameter of blood in a blood vessel comprising a transmitter which is configured to couple a first transmission signal with a first frequency and a second transmission signal with a second frequency into the blood vessel, a receiver which is configured to receive a first reception signal at the first frequency and a second reception signal at the second frequency, and a loss detector which is configured to ascertain a first loss variable on the basis of the first transmission signal and the first reception signal at the first frequency, and a second loss variable on the basis of the second transmission signal and the second reception signal at the second frequency, and also a processor, which is configured to ascertain a first frequency shift of the first loss variable relative to a first reference loss variable, to ascertain a second frequency shift of the second loss variable relative to a second reference loss variable and to ascertain the blood picture parameter on the basis of the first frequency shift and the second frequency shift. By way of example, the loss variables can be electromagnetic loss variables.

By way of example, the first reference loss variable and the second reference loss variable can be determined in advance on the basis of experiments or measurements. By way of example, if the first loss variable and the second loss variable are absorptions of electromagnetic energy, the first reference loss variable and the second reference loss variable can, for example, be absorptions of electromagnetic energy by a reference water solution with a concentration of a blood constituent, e.g. blood sugar.

In accordance with one embodiment, the invention relates to a detection device which furthermore comprises a storage medium for providing the first reference loss variable and the second reference loss variable. As explained above, the reference loss variables can, for example, be established in advance in the laboratory and stored.

In accordance with one embodiment, the invention relates to a detection device, wherein the first loss variable can be an absorption line of a water solution with a blood constituent at the first frequency and wherein the second loss variable can be an absorption line of the water solution at the second frequency. If the blood constituent is blood sugar, absorption lines, for example with absorption maxima or absorption minima, the frequency positions of which depend on the concentration of the blood sugar, are created at different frequencies. The blood picture parameter can be ascertained from the frequency shifts of the absorption lines with respect to reference absorption lines, which can be formed by the aforementioned reference loss variables.

In accordance with one embodiment, the invention relates to a detection device, wherein the first loss variable and the second loss variable define a frequency-dependent profile of absorptions of a water solution with a blood constituent and wherein the first reference variable and the second reference variable define a frequency-dependent profile of absorption lines of the water solution with a reference concentration of the blood constituent.

In accordance with one embodiment, the invention relates to a detection device, wherein the first loss variable is an absorption minimum or an absorption maximum in a first frequency range comprising the first frequency and wherein the second loss variable is an absorption minimum or an absorption maximum in a second frequency range comprising the second frequency.

In accordance with one embodiment, the invention relates to a detection device, wherein the blood picture parameter is a concentration of a blood constituent, in particular sugar such as glucose, or of lactate or lactic acid or of oxygen in the blood.

In accordance with one embodiment, the invention relates to a detection device, wherein the first frequency and the second frequency respectively lie in a frequency range between 1 GHz and 15 GHz.

In accordance with one embodiment, the invention relates to a detection device, wherein the loss detector is configured to ascertain the first loss variable and the second loss variable by means of a two-port measurement.

In accordance with one embodiment, the invention relates to a detection device, wherein the loss detector comprises a network analyzer, in particular a vector or scalar network analyzer, or a power detector.

In accordance with one embodiment, the invention relates to a detection device, wherein the loss detector is configured to ascertain in each case a forward transmission factor $S_{21}$ and/or an input reflection factor $S_{11}$ in order to ascertain the first loss variable and the second loss variable.

In accordance with one embodiment, the invention relates to a detection device, wherein the loss detector is configured to ascertain in each case the first loss variable and the second loss variable on the basis of the following formula:

$$P_{loss} = 1 - |S_{11}|^2 - |S_{21}|^2,$$

where $P_{loss}$ denotes the respective loss variable, and where $S_{11}$ denotes the input reflection factor and $S_{21}$ denotes the forward transmission factor.

In accordance with one embodiment, the invention relates to a detection device, wherein the transmitter for coupling-in the first transmission signal or the second transmission signal comprises at least one transmission antenna, in particular a dipole antenna, a frame antenna or a patch antenna, and wherein the receiver for receiving the first reception signal and the second reception signal comprises at least one reception antenna, in particular a dipole antenna, a frame antenna or a patch antenna, which can be at a distance from the transmission antenna.

In accordance with one embodiment, the invention relates to a detection device, wherein the transmitter is configured to couple the first transmission signal or the second transmission signal into the blood vessel as a mode or a wave type, in particular as a transverse electric (TE) wave or as a transverse magnetic (TM) wave or as a transverse electromagnetic (TEM) wave or as an HE wave, in particular longitudinally or transversely with respect to a flow of the blood vessel.

In accordance with one embodiment, the invention relates to a detection device, wherein the transmitter is configured to couple the first transmission signal and the second transmission signal into the blood vessel successively, in particular by means of a transmission signal generator or of a tunable oscillator, or simultaneously, in particular by means of a broadband signal comprising the first transmission signal and the second transmission signal.

In accordance with a further aspect, the invention relates to a method for detecting a blood picture parameter of blood in a blood vessel, comprising the steps of coupling a first transmission signal with a first frequency into the blood vessel, coupling a second transmission signal with a second frequency into the blood vessel, receiving a first reception signal at the first frequency, receiving a second reception signal at the second frequency, establishing a first loss variable on the basis of the first transmission signal and the first reception signal at the first frequency, establishing a second loss variable on the basis of the second transmission signal and the second reception signal at the second frequency, ascertaining a first frequency shift of the first loss variable relative to a first reference loss variable, ascertaining a second frequency shift of the second loss variable relative to a second reference loss variable, and ascertaining the blood picture parameter on the basis of the first frequency shift and the second frequency shift.

Further method steps emerge directly from the functionality of the detection device for detecting a blood picture parameter.

Further exemplary embodiments will be explained in more detail with reference to the attached drawings. In detail:

FIG. 1 shows a block diagram of a detection device;
FIG. 2 shows a model of a cross-section of a human forearm;
FIGS. 3A to 3D show antennas;
FIG. 4A shows an electric dipole antenna;
FIG. 4B shows an excitation arrangement;
FIG. 5A to 5B show excitation arrangements;
FIG. 6A shows a loop antenna;
FIG. 6B shows an excitation arrangement;
FIG. 7 shows an excitation arrangement;
FIG. 8 shows an excitation arrangement;
FIG. 9 shows an excitation arrangement;
FIG. 10 shows an excitation arrangement;
FIG. 11 shows a basic circuit diagram of a detection device;
FIG. 12 shows a frequency shift of an absorption maximum;
FIG. 13 shows transmission behaviors;
FIG. 14 shows frequency shifts;
FIG. 15 shows a diagram of a method for detecting a blood picture parameter;
FIG. 16 shows a basic circuit diagram of a detection device;
FIG. 17 shows a block diagram of an armband;
FIG. 18 shows a block diagram of a section of an armband;
FIG. 19 shows a block diagram of an armband; and
FIG. 20 shows a block diagram of an arrangement of the electrodes of the detection device.

BRIEF DESCRIPTION OF THE DRAWINGS

Further exemplary embodiments will be explained in more detail with reference to the attached drawings. In detail.

DETAILED DESCRIPTION

Figure 1:
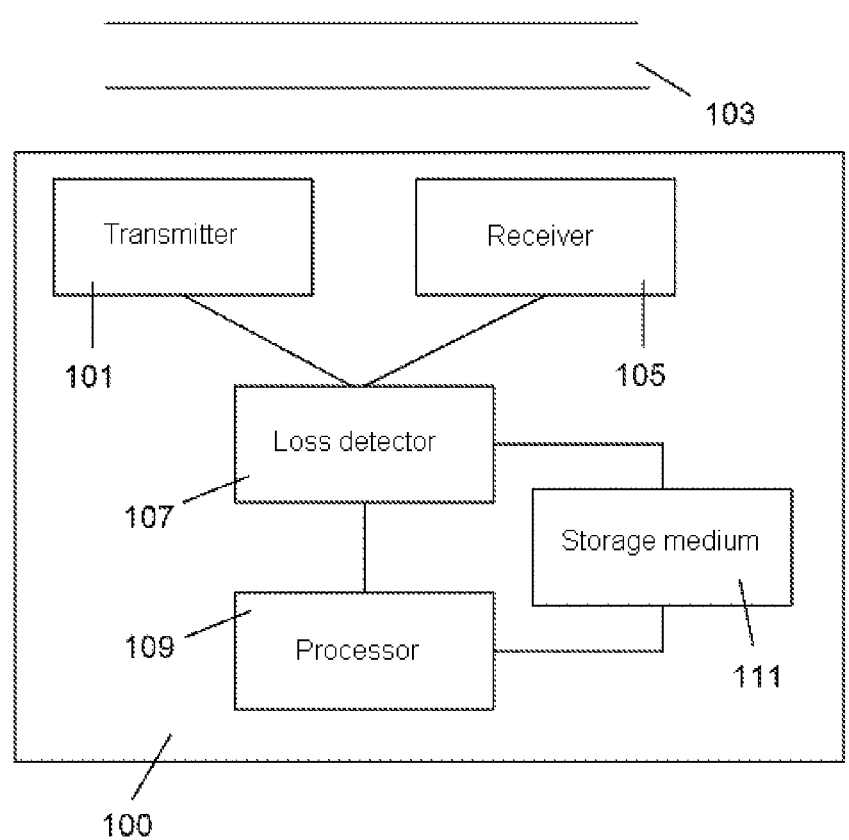
FIG. 1 shows a block diagram of a detection device.

FIG. 1 shows a block diagram of a detection device 100 for detecting a blood picture parameter such as, for example, a concentration of blood sugar. The detection device 100 comprises a transmitter 101, which is configured to couple a first transmission signal with a first frequency and a second transmission signal with a second frequency into the blood vessel 103 illustrated schematically in FIG. 1. By way of example, together, the first transmission signal and the second transmission signal can result in a broadband signal. The transmitter 101 can be configured to emit, one after the other, the first transmission signal and the second transmission signal, for example by a frequency sweep. To this end, the transmitter 101 can have one or more transmission antennas, which can, for example, be embodied as dipole antennas or frame antennas or patch antennas.

The detection device 100 furthermore comprises a receiver 105, which is configured to receive a first reception signal at the first frequency and a second reception signal at the second frequency. To this end, the receiver 105 can have one or more reception antennas.

The detection device 100 furthermore comprises a loss detector 107, which, for example, is coupled to the transmitter 101 and the receiver 105 and is provided for ascertaining a first loss variable on the basis of the first transmission signal and the first reception signal and also a second loss variable on the basis of the second transmission signal and the second reception signal.

The detection device furthermore comprises a processor 109, which is coupled to the loss detector 107 and is provided for ascertaining a first frequency shift of the first loss variable relative to a first reference loss variable and a second frequency shift of the second loss variable relative to a second reference loss variable. The processor 109 can furthermore be configured to ascertain the blood picture parameter on the basis of the two frequency shifts.

The detection device 100 can furthermore have a storage medium 111, which can be accessed by, for example, the processor 109 and, optionally, the loss detector 107. By way of example, the first and the second reference loss variable or a plurality of reference loss variables are stored in the storage medium 111. By way of example, the reference loss variables can be absorptions or absorption lines of a water solution with a blood constituent, for example blood sugar. The loss variables detected on the basis of the frequency shifts can be frequency-shifted absorptions or absorption lines such that the blood picture parameter, such as, for example, a concentration of blood sugar, can be established on the basis of the frequency shifts.

The detection device 100 illustrated in FIG. 1 uses the discovery that a blood vessel, a layer of skin and fatty tissue surrounding the blood vessel of, for example, a human forearm can be considered to be a dielectric waveguide system. The makeup of a human forearm is described, for example, in Netter, F. N. "Atlas der Anatomie" [Anatomical Atlas], Thieme Verlag, 2006. A human forearm consists of two bones which are surrounded by muscular tissue. Distributed around the muscular tissue are surface veins, i.e. blood vessels. The bones, the muscular tissue and the veins are encapsulated by fatty tissue, which is covered by upper layers of skin. The surface veins are arranged relatively close to the upper layers of skin and separated therefrom by the fatty tissue. By way of example, if the transmitter 101 and the receiver 105, illustrated in FIG. 1, are placed onto the upper layer of skin, the transmitter 101 can be used to couple e.g. a transverse electric (TE) wave or a transverse magnetic (TM) wave into the dielectric waveguide system formed by a blood vessel, fatty tissue and a layer of skin. Here, the layer of skin and the fatty tissue can be understood to be a thin-film waveguide.

By way of example, if use is made of a microwave measurement head, as can be employed for ascertaining a complex relative permittivity of materials, it is possible thereby to characterize the substance mixture consisting of skin, fatty tissue and veins.

In order to detect a blood picture parameter, it is advantageous to detect substantially only the venous blood. To this end, the transmitter 101 can be configured to couple the transmission signal in the form of an electromagnetic wave directly into the blood vessel 103. The transmitter 101 and the receiver 105 can each have a plurality of antennas such that, for the purposes of coupling the electromagnetic wave into the blood vessel 103 and decoupling an electromagnetic wave from the blood vessel, it is in each case possible to select that transmission antenna and reception antenna which are connected with the smallest coupling losses.

Figures 2A, 2B, 2C:
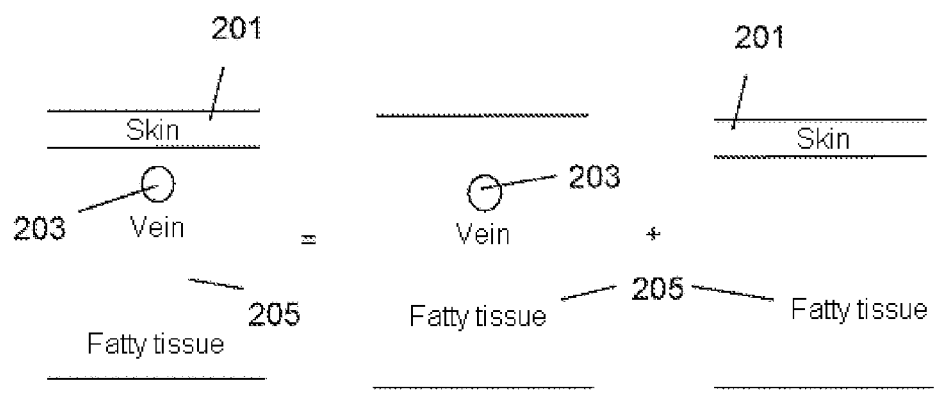
FIG. 2 shows a model of a cross-section of a human forearm.

FIGS. 2A to 2C illustrate a simplified model of a cross-section of a human forearm, e.g. of a wrist, as can be employed, for example, for field simulations or for modeling a dielectric waveguide system. As illustrated in FIG. 2A, the model comprises a layer of skin 201, a blood vessel 203 and fatty tissue 205 surrounding the blood vessel 203. The model illustrated in FIG. 2A forms a dielectric waveguide system comprising the dielectric waveguide illustrated in FIG. 2B and the electrical thin-film waveguide illustrated in FIG. 2C.

The dielectric waveguide illustrated in FIG. 2B comprises the blood vessel 203 and the fatty tissue 205 surrounding the latter. The dielectric thin-film waveguide from FIG. 2C comprises the layer of skin 201 and the fatty tissue 205. A different dispersive, i.e. frequency dependent, behavior of the respective complex relative permittivity can be attached in each case to the layer of skin 201, to the fatty tissue 205 and to the blood vessel 203. Here, the blood vessel 203 lying at the top is interpreted as a dielectric waveguide, in which, depending on the frequency, different modes or wave types, for example a TE wave, a TM wave, a TEM wave or an HE wave, are able to propagate. Added to the waveguide mechanism in the dielectric waveguide, there is an additional waveguide mechanism in the form of the thin-film waveguide illustrated in FIG. 2C, which is formed by the upper layer of skin 201.

A transmission antenna of the transmitter 101 and a reception antenna of the receiver 105 can preferably be configured in such a way that they couple microwave power into the blood vessel 203 in a dedicated fashion and decouple said microwave power again after, for example, a few centimeters. Here, the blood vessel 203 serves as a measurement length and should therefore be considered as a distributed element and no longer as a concentrated element. The measurement of the loss variables is preferably carried out on the basis of a two-port measurement. Here, particularly when coupling the detection device to a wrist, primary modes can be excited in the dielectric waveguide 2B such that an excitation of thin-film waveguide modes in the thin-film waveguide 2C is avoided, as a result of which the blood picture parameter can be detected more accurately.

In order to excite primary modes in the dielectric waveguide system, it is possible to take into account that, depending on the selected frequency of a transmission signal, different modes can be dominant. It is preferable for mode types, which have a concentration of the fields in the blood vessel 203, to be preferred over those modes in which the fields are concentrated in the layer of skin 201. What is shown on the basis of the dielectric properties of the dielectric waveguide illustrated in FIG. 2B is that for certain types of modes longitudinal components $E_{longitudinal}$, $H_{longitudinal}$ are stronger in the propagation direction, i.e. in the direction of a blood vessel extent, than the transverse components $E_{transverse}$, $H_{transverse}$, i.e. transverse to the blood vessel extent. Therefore those modes which enable maximum coupling of the microwave power into the blood vessel 203 are preferably excited in the frequency range to be detected.

FIGS. 3A to 3D illustrate some antennas in an exemplary fashion, which antennas can be used as transmission antennas, i.e. excitation means, or else as reception antennas.

Figure 3A:
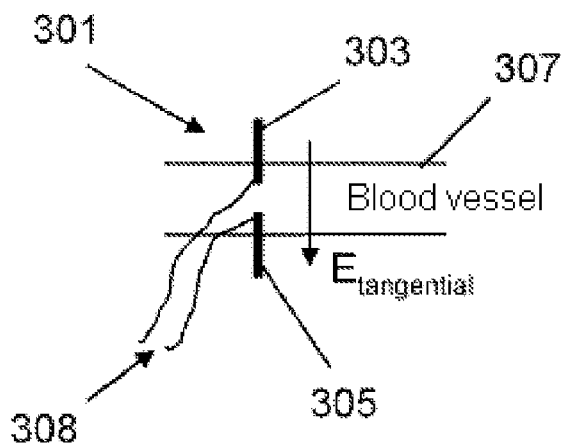
FIGS. 3A, 3D show antennas.

The antenna 301 illustrated in FIG. 3A is configured as an electric dipole with a first antenna section 303 and a second antenna section 305. The antenna sections 303 and 305 are distanced from one another and are arranged, for example, transversely with respect to the extent of a blood vessel 307. The antenna 301 can be excited by supply lines 308. An electric dipole arranged in this manner can, for example, generate an electric field $E_{tangential}$, which points across the extent of the blood vessel or across the blood flow direction.

Figure 3B:
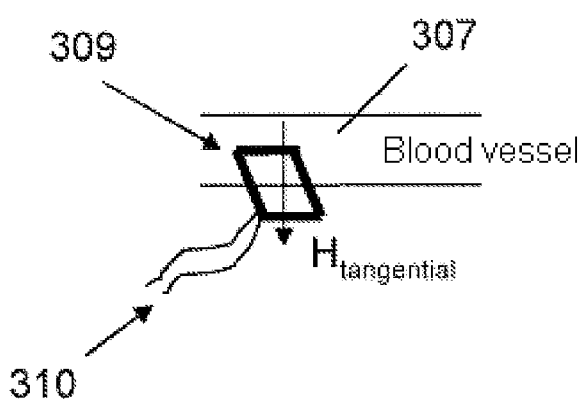

FIG. 3B illustrates an antenna 309, which can be a frame antenna. By way of example, the frame antenna can have a quadrilateral or round shape. In the arrangement of the frame antenna 309 with respect to the blood vessel 307 illustrated in FIG. 3B, e.g. a magnetic field H$_{tangential}$ is excited, which points across the extent of the blood vessel 307 or across the blood flow direction. The antenna 309 can be excited by supply lines 310.

Figure 3C:
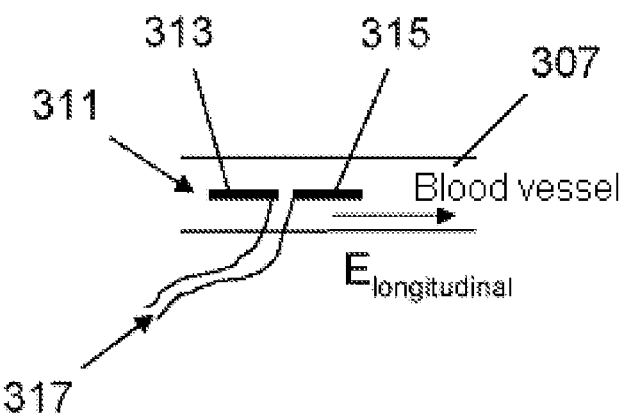

FIG. 3C illustrates an antenna 311, which forms an electric dipole with a first antenna section 313 and a second antenna section 315. The antenna sections 313 and 315 are distanced from one another and are excited by means of the supply lines 317 illustrated in FIG. 3C. The electric dipole formed by the antenna 311 is arranged in such a way with respect to the extent of the blood vessel 307 that the sections 313 and 315 are arranged parallel to the extent of the blood vessel 307. As a result of this, an electric field with the field component E$_{longitudinal}$, which electric field points in the direction of the extent of the blood vessel, is excited.

Figure 3D:
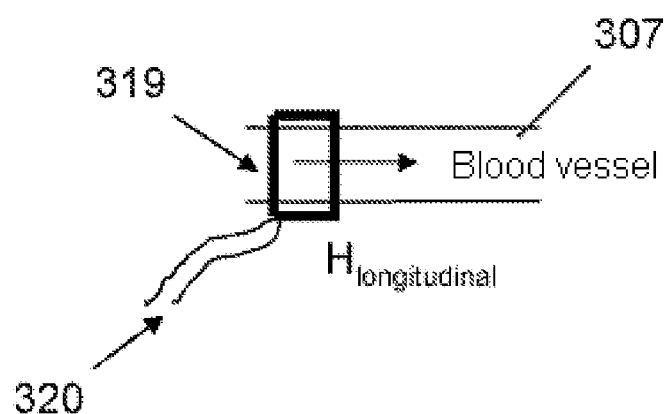

FIG. 3D shows a frame antenna 319, which can, for example, be formed in the form of a quadrilateral or round frame, which forms a loop antenna, for example as a patch antenna. The frame antenna 319 is excited by means of supply lines 320 and is, as illustrated in FIG. 3D, arranged in such a way with respect to the extent of the blood vessel 307 or with respect to the blood flow direction that the magnetic field has a component H$_{longitudinal}$ pointing in the direction of the extent of the blood vessel 307.

By way of example, the frequency range to be measured in each case conforms to which spectral lines, i.e. which absorption lines, should be detected. By way of example, it is possible to observe the characteristic absorption lines of a substance or else an effect which a specific blood constituent has on the absorption lines of water or of a water solution with a concentration of the blood constituent.

The antennas illustrated in FIGS. 3A to 3D are either electric dipoles or magnetic frame antennas. Moreover, use can also be made of patch antennas. Electric dipoles dominantly produce an electric field along the axis of the electric dipole. This axis can either, as illustrated in FIG. 3A, be aligned tangentially with respect to the blood vessel 307 or the blood flow direction or, as illustrated in FIG. 3C, be aligned in the direction of the blood vessel 307 or in the blood flow direction. If it is primarily a magnetic field that should be generated, a frame antenna can be used as excitation means. If a surface vector on the surface spanned by the frame forming the frame antenna is aligned across the blood vessel 307 or across the blood flow direction, the magnetic field is also aligned across the blood vessel 307, as illustrated in FIG. 3B. By contrast, if the surface vector points in the direction of the blood vessel 307, the magnetic field is also aligned in the direction of the blood vessel 307, as is illustrated in, for example, FIG. 3B. The selection of an excitation means illustrated in FIGS. 3A to 3D then results in, for example, the dominant excited mode or wave type.

Figure 4A:
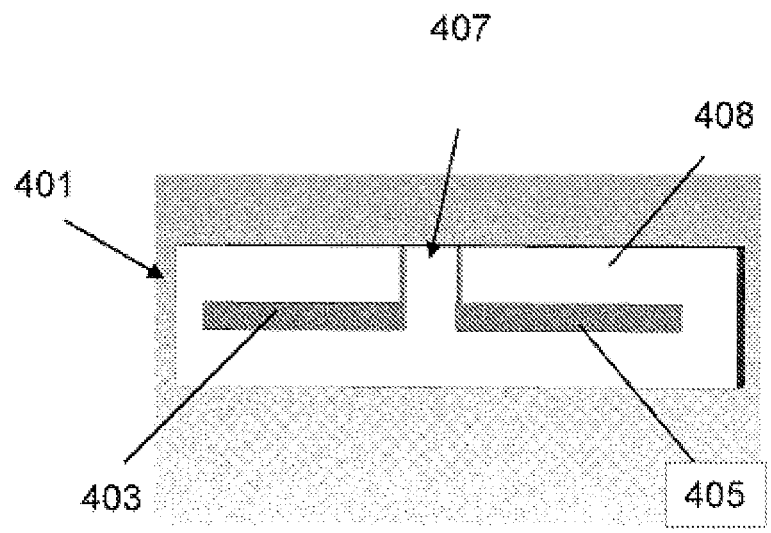
FIG. 4A shows an electric dipole antenna.

FIG. 4A shows an electric dipole antenna 401, which can be used as a transmission antenna or as a reception antenna. The electric dipole antenna 401 comprises dipole antenna sections 403 and 405, which are arranged in or on a substrate 408 and can be excited by means of supply lines 407. The dipole antenna 401 can be used as a transmission antenna or as a reception antenna.

Figure 4B:
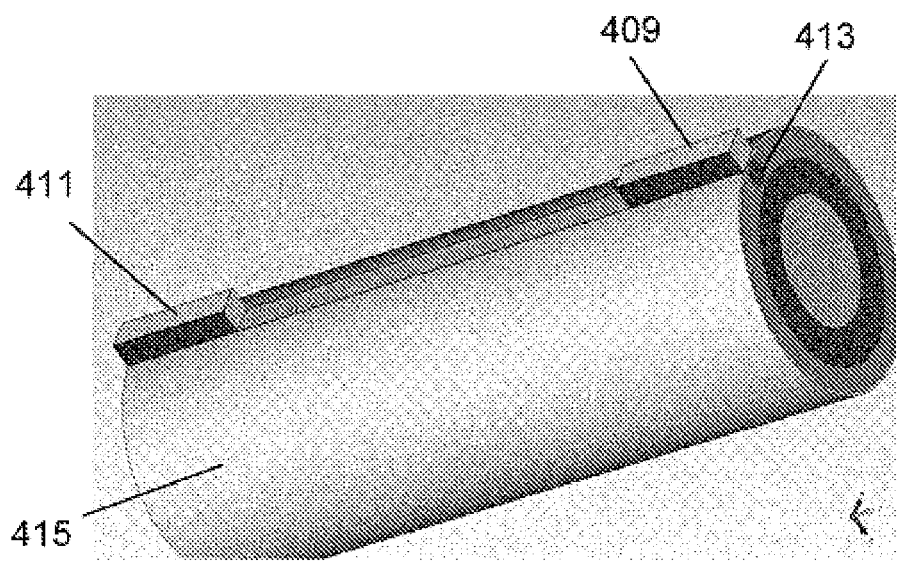
FIG. 4B shows an excitation arrangement.

FIG. 4B shows an excitation arrangement of a transmission antenna 409 of a transmitter and of a reception antenna 411 of a receiver in the direction of an extent of a blood vessel 413 below a layer of skin 415. The transmission antenna 409 and the reception antenna 411 are, for example, electric dipole antennas in accordance with FIG. 4A. In the arrangement illustrated in FIG. 4B, an electric field with a field component in the direction of the extent of the blood vessel 413, or in the blood flow direction, is generated.

Figure 5A:
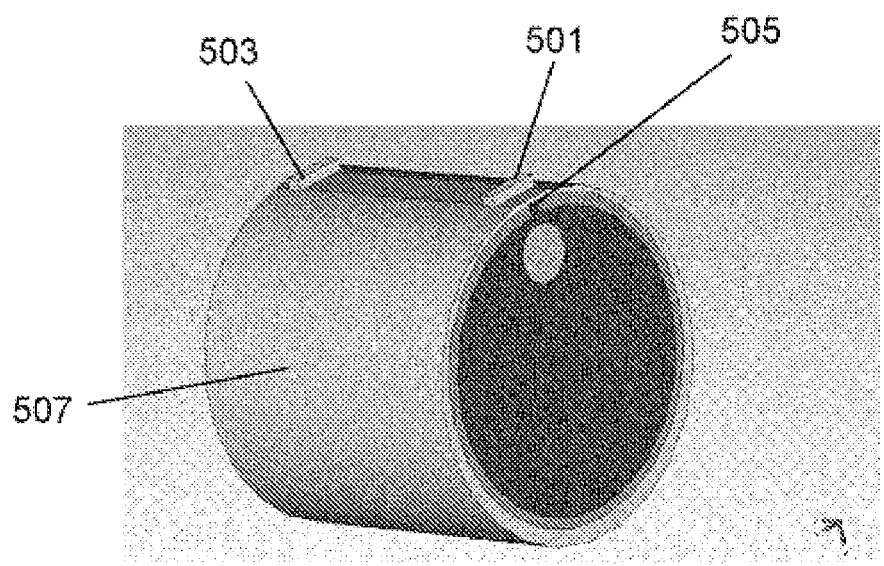
FIGS. 5A to 5B show excitation arrangements.
Figure 5B:
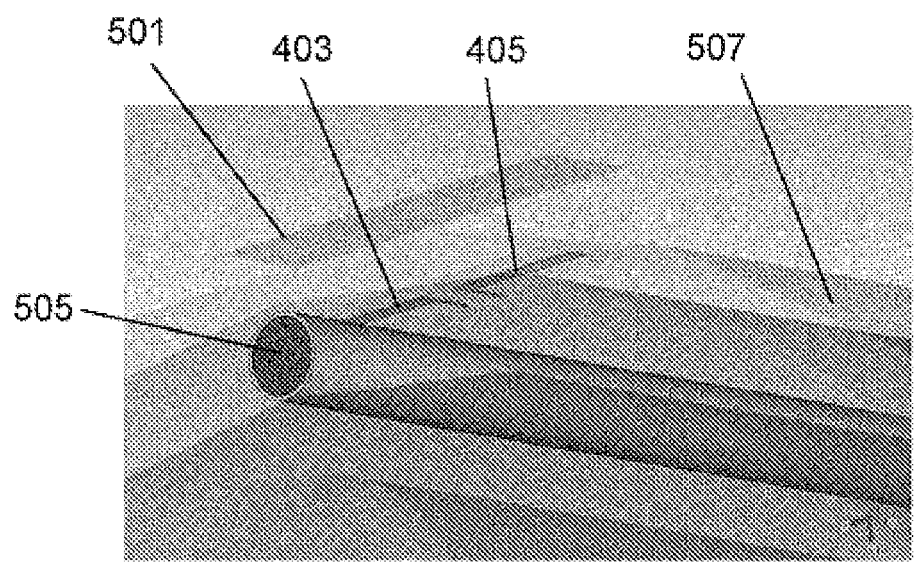

FIG. 5A shows an excitation arrangement comprising a transmission antenna 501 of a transmitter and a reception antenna 503 of a receiver, across the direction of extent of a blood vessel 505, i.e. across the blood flow direction, which lies under a layer of skin 507. The transmission antenna 501 and the reception antenna 503 can each be formed by e.g. the electric dipole antenna illustrated in FIG. 4A. In FIG. 5B, the arrangement of the dipole antenna sections 403 and 405 is illustrated in more detail in respect of the blood flow direction.

Figure 6A:
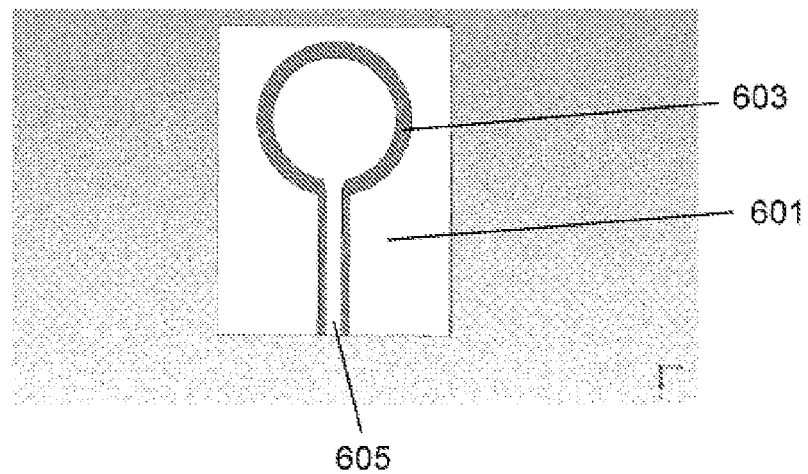
FIG. 6A shows a loop antenna.

FIG. 6A shows a loop antenna 601 with a circular frame 603 and supply lines 605 for exciting the circular frame 603. The loop antenna 601 can, for example, be used as a transmission antenna or as a reception antenna. The circular frame 603 and the supply lines 605 can be arranged in or on a substrate.

Figure 6B:
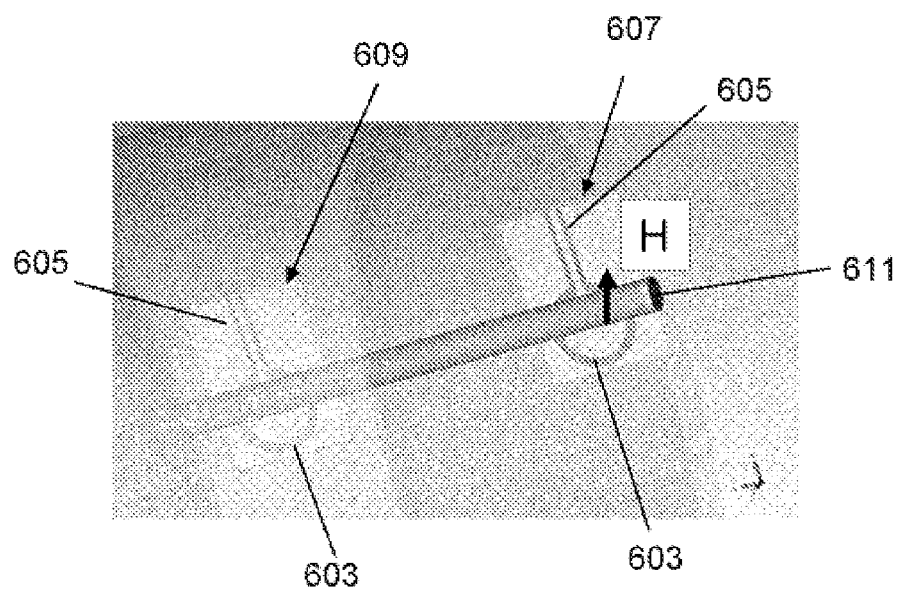
FIG. 6B shows an excitation arrangement.

FIG. 6B shows an excitation arrangement with a transmission antenna 607 of a transmitter and a reception antenna 609 of a receiver, which can be formed as loop antennas as per FIG. 6A. By way of example, the loop antennas 607, 609 are arranged in such a way that the circular frames 603 are arranged above a blood vessel 611, with the supply lines 605 pointing across the extent of the blood vessel 611, i.e. across the blood flow direction. As a result of this, a magnetic field with a component H of the magnetic field pointing across the extent of the blood vessel 611 is generated on the transmitter side.

Figure 7:
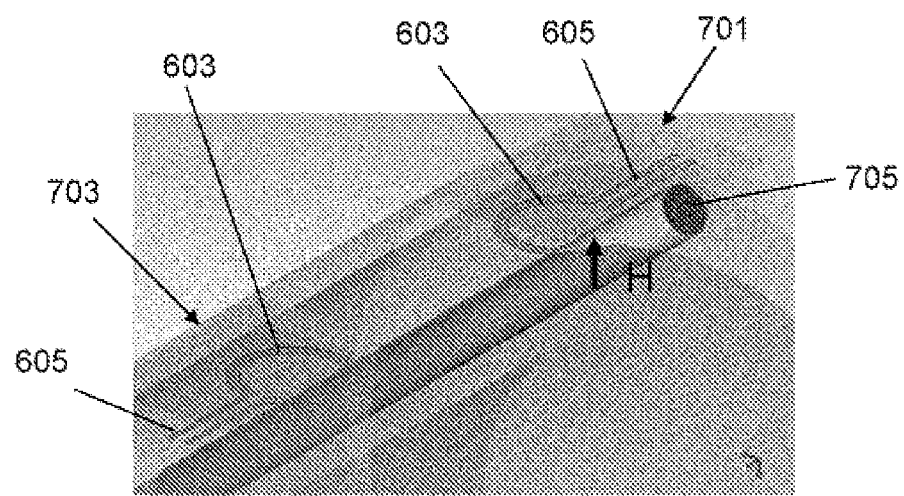
FIG. 7 shows an excitation arrangement.

FIG. 7 shows an excitation arrangement of a transmission antenna 701 of a transmitter and a reception antenna 703 of a receiver, with respect to a blood vessel 705. By way of example, the transmission antenna 701 and the reception antenna 703 can be loop antennas with that shape illustrated in FIG. 6A. By way of example, they are arranged in such a way that the circular frames 603 are respectively arranged above the blood vessel 705 and that the supply lines 605 extend pointing away from one another, parallel to the extent of the blood vessel 705. As a result of this, a magnetic field component H pointing perpendicular to the extent of the blood vessel 705 is generated, which field component points in the direction of a normal of the surface spanned by the circular frame 603.

Figure 8:
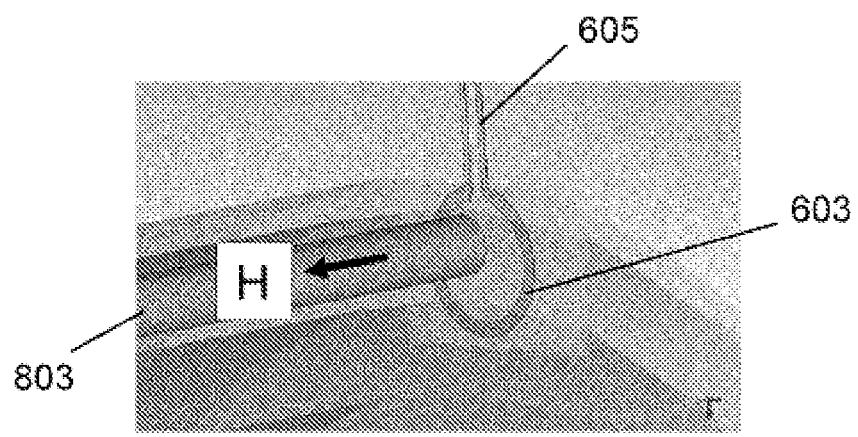
FIG. 8 shows an excitation arrangement.

FIG. 8 shows an excitation arrangement with a transmission antenna 801 of a transmitter, which, for example, has the shape of a loop antenna illustrated in FIG. 6A. By way of example, the transmission antenna 801 is arranged in such a way with respect to a blood vessel 803 that a normal of the surface spanned by the frame 603 points in the direction of the extent of the blood vessel 803. By way of example, such an arrangement can be realized at a bend in the blood vessel 803. As a result of this, a magnetic field component H pointing in the direction of the extent of the blood vessel 803 is generated.

Figure 9:
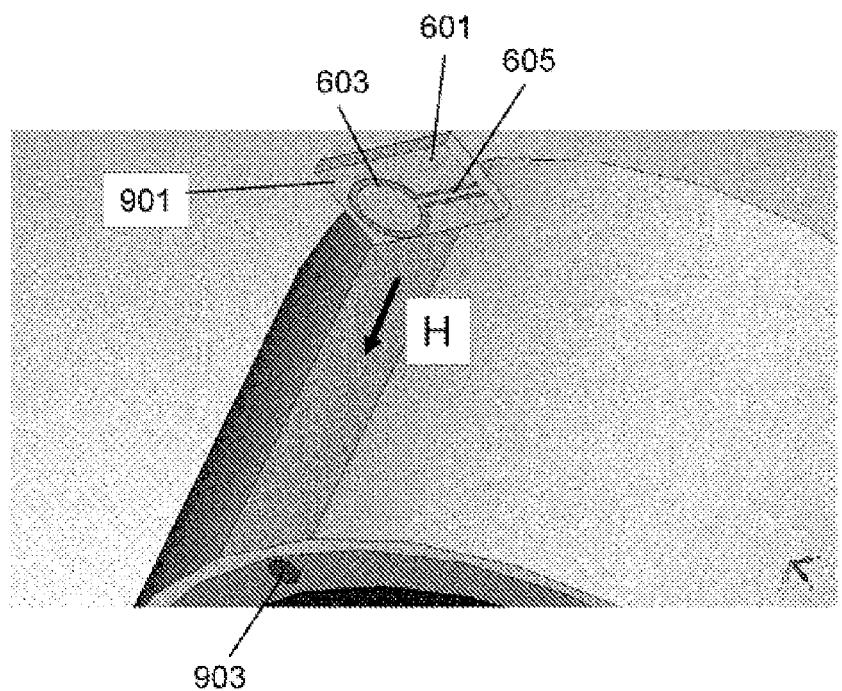
FIG. 9 shows an excitation arrangement.

FIG. 9 shows an excitation arrangement with a transmission antenna 601, which, for example, is a loop antenna with the shape illustrated in FIG. 6A and can be arranged in or on a substrate 901, for example a polymer substrate. The transmission antenna 601 is arranged above a blood vessel 903 in such a way that a normal of the surface spanned by the circular frame 603 points in the direction of the extent of the blood vessel 903. As a result of this, a magnetic field is generated with a magnetic field component H pointing in the direction of the extent of the blood vessel 903, i.e. in the blood flow direction.

Figure 10:
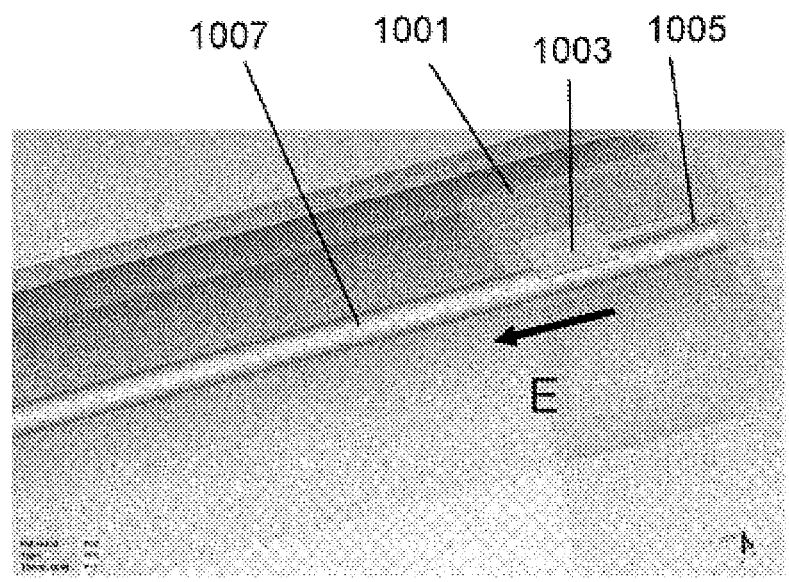
FIG. 10 shows an excitation arrangement.

FIG. 10 shows an excitation arrangement with a transmission antenna 1001, which can be a patch antenna with a patch antenna surface 1003 and supply lines 1005. The patch antenna surface 1003 is, for example, arranged above a blood vessel 1007, as a result of which an electric field is generated with an electric field component E pointing in the direction of an extent of the blood vessel 1007, i.e. in the blood flow direction.

In accordance with a further embodiment, the loss detector 107 is configured to carry out e.g. a scalar or a vector measurement or a power measurement. In order to ascertain the loss variables, a simple spectroscopic measurement can be carried out, in which the absolute value of the measurement parameter S21 is detected.

Figure 11:
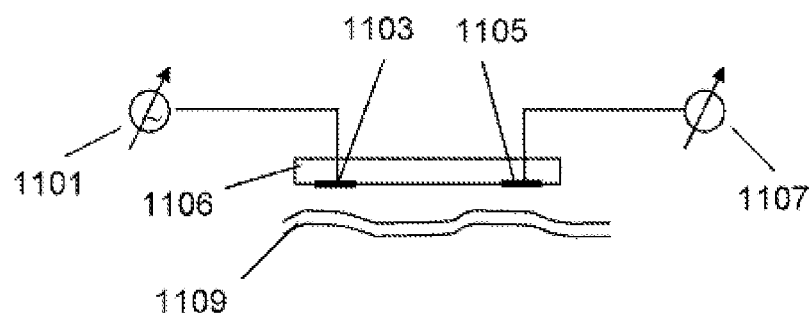
FIG. 11 shows a basic circuit diagram of a detection device.

By way of example, $|S_{21}|$ can be measured by means of the detection device illustrated in FIG. 11. The detection device comprises a transmitter with a transmission signal generator 1101, which can be a tunable oscillator. An output of the transmission signal generator 1101 is connected to a transmission antenna 1103. The detection device furthermore comprises a receiver with a reception antenna 1105, the output of which is connected to a loss detector 1107. By way of example, the loss detector can comprise a power detector. As illustrated in FIG. 11, the transmission antenna 1103 and the reception antenna 1105 are arranged above a blood vessel 1109. The transmitter can have features of the transmitter 101, the receiver can have features of the receiver 105 and the loss detector 1107 can have features of the loss detector 107.

The accuracy when ascertaining the loss variables, i.e. the losses in the waveguide, can be increased further by a further measurement of an absolute value of the measurement parameter S11. By way of example, the loss variables can be ascertained on the basis of the following formula:

$$P_{loss} = 1 - |S_{11}|^2 - |S_{21}|^2,$$

where $P_{loss}$ denotes the respective loss variable and where $S_{11}$ denotes the input reflection factor and $S_{21}$ denotes the forward transmission factor.

Figure 12:
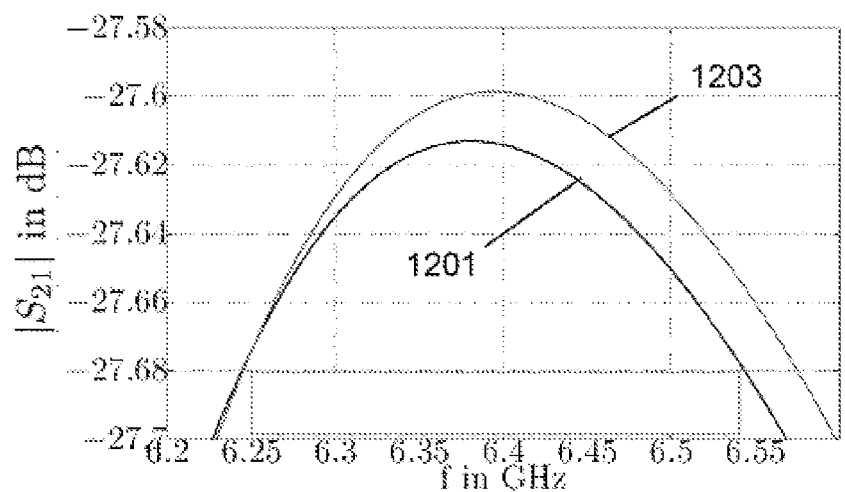
FIG. 12 shows a frequency shift of an absorption maximum.

In order to detect the blood picture parameter, for example a concentration of blood sugar, frequency shifts of the absorption lines of a water solution with sugar can, for example, be examined. By way of example, FIG. 12 shows a frequency shift of an absorption maximum 1201 at a first blood sugar concentration compared to a frequency shift of an absorption maximum 1203 at a second blood sugar concentration, which is higher than the first blood sugar concentration. Here, a transmission around 6 GHz was detected in an exemplary fashion as loss variable.

The frequency shift of the absorption maximum can be considered to be a measure for a blood picture parameter, for example for a blood sugar level. By observing frequency shifts in a number of absorptions of a water solution with sugar, the measurement reliability can be increased still further.

Figures 13, 14:
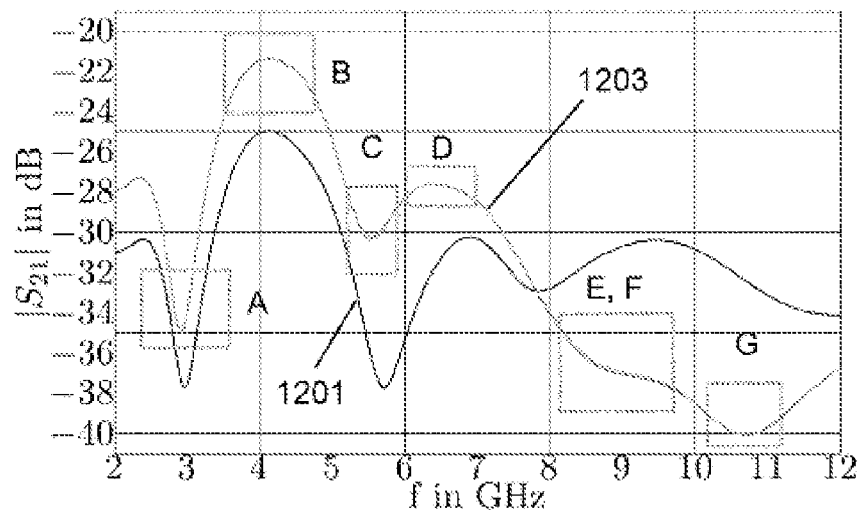
FIG. 13 shows transmission behaviors.
FIG. 14 shows frequency shifts.

FIG. 13 shows transmission behaviors of venous blood in a wrist. Here, the profiles 1301 and 1303 clarify different frequency positions of absorption lines at different blood sugar concentrations. In order to detect the blood picture parameter, such as, for example, the concentration of the blood sugar, it is possible, for example, to detect frequency shifts of the absorptions A, B, C, D, E, F and G in a targeted manner. Thus, it is possible, for example, to observe a shift in the direction of higher or lower frequencies depending on blood sugar level, for example in a frequency range between 2 GHz and 12 GHz, for each frequency of an absorption maximum and/or an absorption minimum.

FIG. 14 shows, in an exemplary fashion, frequency shifts of the absorptions A, B, C, D, E, F and G illustrated in FIG. 13 for a blood vessel with a diameter of 6 mm and for a blood vessel with a diameter of 3.4 mm. It is possible to identify that the absorptions for a sugar level variation can have frequency shifts in both positive and negative directions. Detecting a plurality of absorptions or absorption lines therefore makes it possible to detect a blood picture parameter, for example the blood sugar level, more accurately.

Figure 15:
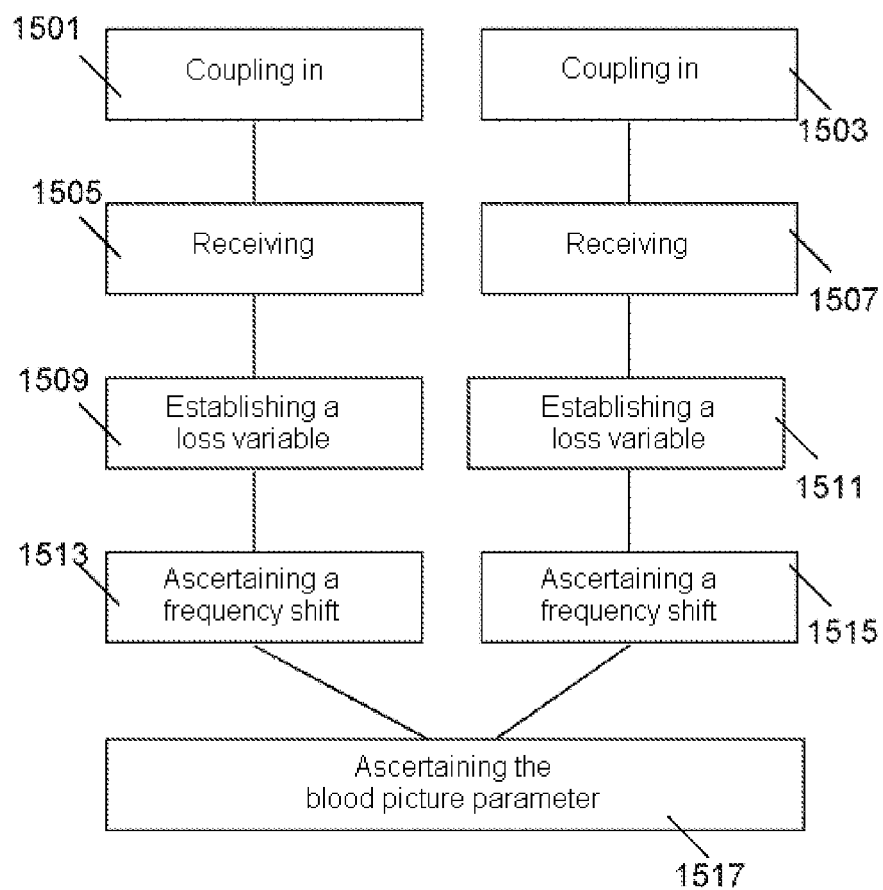
FIG. 15 shows a diagram of a method for detecting a blood picture parameter.

FIG. 15 shows a diagram of a method for detecting a blood picture parameter of blood in a blood vessel. The method comprises a first transmission signal with a first frequency being coupled 1501 into the blood vessel, a second transmission signal with a second frequency being coupled 1503 into the blood vessel, a first reception signal being received 1505 at the first frequency, a second reception signal being received 1507 at the second frequency, a first loss variable being established 1509 on the basis of the first transmission signal and the first reception signal at the first frequency, a second loss variable being established 1511 on the basis of the second transmission signal and the second reception signal at the second frequency, a first frequency shift of the first loss variable being ascertained 1513 relative to a first reference loss variable, a second frequency shift of the second loss variable being ascertained 1515 relative to a second reference loss variable and the blood picture parameter being ascertained 1517 on the basis of the first frequency shift and the second frequency shift.

By way of example, the method illustrated in FIG. 15 can be executed by the detection device illustrated in FIG. 1 or in FIG. 11.

The aforementioned detection principle can, for example, be integrated into an armband, which can be placed around a wrist and, for example, be pumped up. As a result of this, the coupling of the electromagnetic waves onto the body becomes reproducible since there is always the same pressure, which minimizes an air gap between a layer of skin and the antennas. The aforementioned principle of the microwave measurement is moreover very robust since it is not the height of the absorption lines but the frequency shift thereof which is detected and evaluated. A blood picture parameter such as, for example, a blood sugar content can be monitored continuously. As a result, it can be rendered possible to ascertain a delay time between food intake and an increase in blood sugar. Moreover, it is possible to react more quickly to variations in a daily routine of a patient. Thus, for example, an alarm can be triggered in the case of too much or too little sugar, with a telemedical link of the detection device, illustrated in FIG. 1 for example, being conceivable.

In accordance with one embodiment, provision can, for targeted microwave coupling into a blood vessel, be made for a number of transmission antennas on the transmission side and a number of reception antennas on the reception side. By means of a permutation of all antenna combinations, it is possible, for example, to select that antenna pair comprising a transmission antenna about a reception antenna which is connected with the smallest coupling-in losses. The selected antenna pair can then be used for microwave-based detection of the blood picture parameter.

By way of example, the transmitter 101, illustrated in FIG. 1, can have one or more transmission antennas for emitting one or more transmission signals, which antennas can, for example, be configured as dipole antennas or frame antennas or patch antennas. Analogously to this, the receiver 105 can have one or more transmission antennas for receiving one or more reception signals. The processor 109 is preferably configured to select a plurality of detection configurations in succession. Here, each detection configuration comprises a single transmission antenna and a single reception antenna, wherein the transmission antennas can be spaced apart from one another and wherein the reception antennas can be spaced apart from one another. When a detection configuration is selected, the transmitter 101 excites the associated transmission antenna to emit a transmission signal, with the receiver 105 using the respective reception antenna to receive a reception signal.

The loss detector 107 can, for example, ascertain an electromagnetic loss variable such as energy absorption on the basis of the transmission signal and the reception signal. In the next step, a further detection configuration is used for emitting a transmission signal and a further loss variable is detected. This is how a plurality of detection configurations are used in succession, or in any sequence, to couple a transmission signal into the blood vessel 103, with a loss variable being ascertained by means of the loss detector 107 in each detection configuration. By way of example, the processor 109 can compare the loss variables and select that detection configuration which is connected with the smallest loss variable. The selected detection configuration is used for detecting the blood picture parameter.

Figure 16:
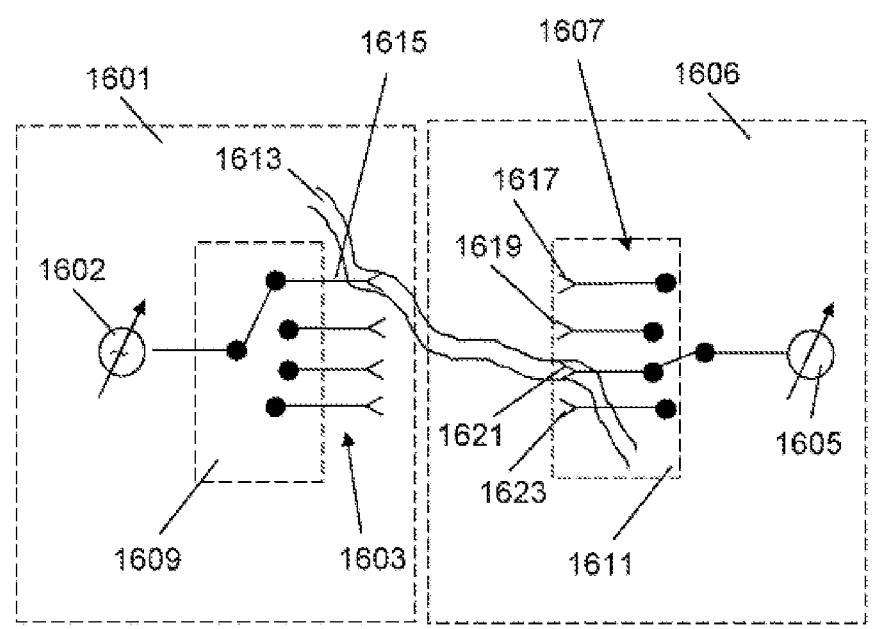
FIG. 16 shows a basic circuit diagram of a detection device.

FIG. 16 shows a detection device which can be an embodiment of the detection device 100 represented in FIG. 1. The detection device comprises a transmitter 1601, which detection device, for example, can have a tunable oscillator 1602 and a plurality of transmission antennas 1603. The detection device furthermore comprises a loss detector 1605, which can, for example, have a power detector. Furthermore, provision is made for a receiver 1606 with a plurality of reception antennas 1607.

One output of the tunable oscillator 1602 can be connected to each antenna input, for example in succession or in any sequence, in a switchable manner, for example by means of a switching matrix 1609. Analogously to this, each output of a reception antenna of the plurality of reception antennas 1607 can be connected to the loss detector 1605 by means of a switching matrix 1611.

By way of example, the switching matrix 1611 and the switching matrix 1609 can be used to select that pair comprising a transmission antenna and a reception antenna which enables optimum coupling of a microwave signal into a blood vessel 1613 illustrated schematically in FIG. 16. The switching matrices 1609 and 1611 are used to select the antenna pairs in succession, starting with, for example, a first transmission antenna 1615 by means of which a transmission signal is emitted.

The switching matrices 1609, 1611 can have switches, for example transistor switches.

On the reception side, the switching matrix 1611 is used to select the reception antennas in succession, starting with, for example, the reception antenna 1617 for receiving a corresponding reception signal, with a loss variable being detected on the basis of the transmission signal and the reception signal. In the next step, the reception antenna 1619 is for example selected, with a loss variable once again being detected by means of the loss detector on the basis of the transmission signal and a reception signal received by the reception antenna 1619. After this, for example, the reception antenna 1621 is selected, with a further loss variable being detected on the basis of the transmission signal and a reception signal. In the next step, the reception antenna 1623 is selected and a further loss variable is ascertained on the basis of the transmission signal and a reception signal received by the reception antenna 1623. In the next step, the switching matrix 1609 can, for example, select a further transmission antenna, wherein the aforementioned steps can be repeated. By a comparison of the established loss variables, the smallest loss variable, for example, is selected. In the example illustrated in FIG. 16, it is to be expected, for example, that the detection configuration with the transmission antenna 1615 and the reception antenna 1621 is afflicted with the smallest coupling-in losses because the antennas 1615, 1621 lie directly above the blood vessel and therefore enable a signal to be coupled into the blood vessel 1613. By way of example, the selected detection configuration can be used for detecting a blood picture parameter. The above-described selection steps can be carried out in any sequence. Thus, for example, all or some of the reception antennas 1607 can be tested for the transmission antenna 1615.

The transmission antennas 1603 or the reception antennas 1607 can differ in respect of their location and/or in respect of their field component which should be excited in a dominant fashion. Here, the switching matrices 1609 and 1611 ensure that the optimal excitation type, for example a loop antenna, an electric dipole antenna, a patch antenna, or excitation location can be selected for the respectively selected frequency.

In accordance with one embodiment, the measurement is carried out in a broadband fashion instead of in a narrowband fashion. By way of example, the transmission signals can be coupled into the blood vessel by means of a frequency sweep or as a partial signal of a broadband transmission signal. As a result of the preferred vectorial detection of the S-parameter, it is now possible to evaluate the complex relative permittivity and not only the real part thereof. By observing frequency shifts of a plurality of absorption lines, the blood picture parameter can be ascertained more accurately. This is preferably carried out by means of a two-port measurement and not by means of a one-port measurement.

Figure 17:
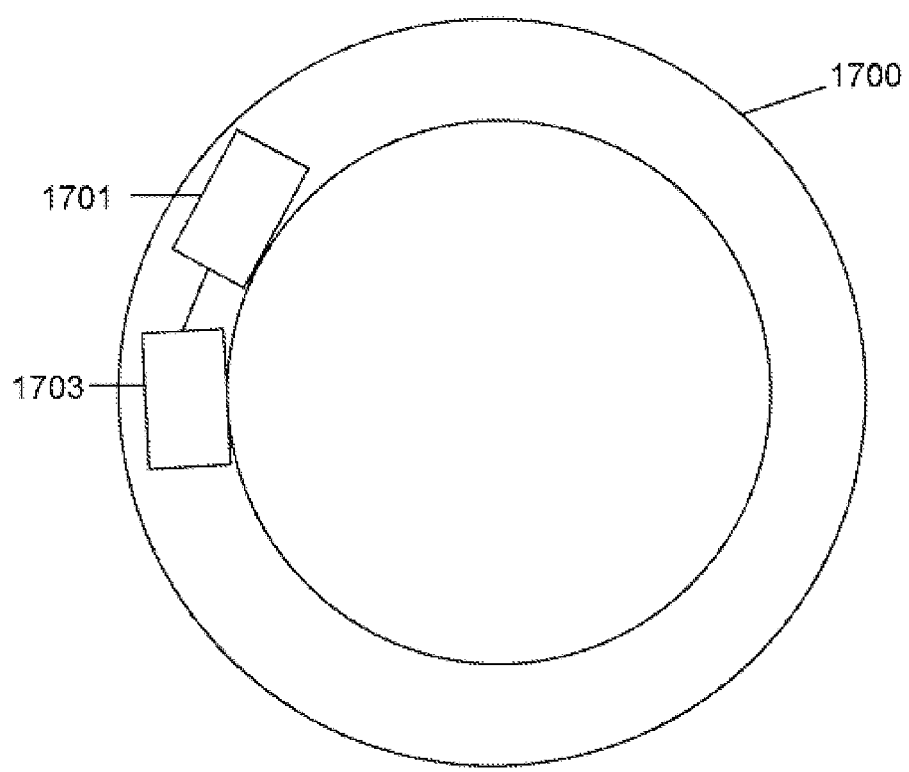
FIG. 17 shows a block diagram of an armband.

FIG. 17 shows a block diagram of an exemplary embodiment of an armband 1900 with a detection device 1701 and a setting device 1703. The detection device 1701 is configured to detect a blood picture parameter of blood in a blood vessel of the arm. An example for the blood picture parameter to be detected is the glucose concentration in the blood.

The setting device 1703 is configured to set a predeterminable contact pressure of the armband 1700 on the arm. By setting the predetermined contact pressure of the armband 1700, the setting device 1703 can ensure reproducible detections of the blood picture parameter by the detection device 1701. To this end, the setting device 1703 is, in particular, configured to set the contact pressure of the armband 1700 to the predeterminable contact pressure when the blood picture parameter is being detected by the detection device 1701.

In particular, the armband 1700 is embodied as an inflatable armband 1700. Here, the setting device 1703 in particular has an air pump, which is configured to inflate the armband 1700 for setting the predetermined contact pressure.

In detail, the detection device 1701 comprises electrodes in particular, which are configured to couple at least a radiofrequency signal into the blood vessel. The radiofrequency signal is configured to supply a parameter for detecting the blood picture parameter. An example for such a parameter is formed by the relaxation time constant T of the blood picture parameter. Here, the setting device 1703 is more particularly designed to set the contact pressure of the electrodes on the arm to the predetermined contact pressure.

Furthermore, the setting device 1703 can be embodied in such a way that it distributes the contact forces of the armband 1700 uniformly on the arm when the blood picture parameter is being detected by the detection device 1701. Furthermore, the setting device 1703 is preferably configured in such a way that it ensures uniform contact of the armband 1700 while the blood picture parameter is being detected by the detection device 1701.

Figure 18:
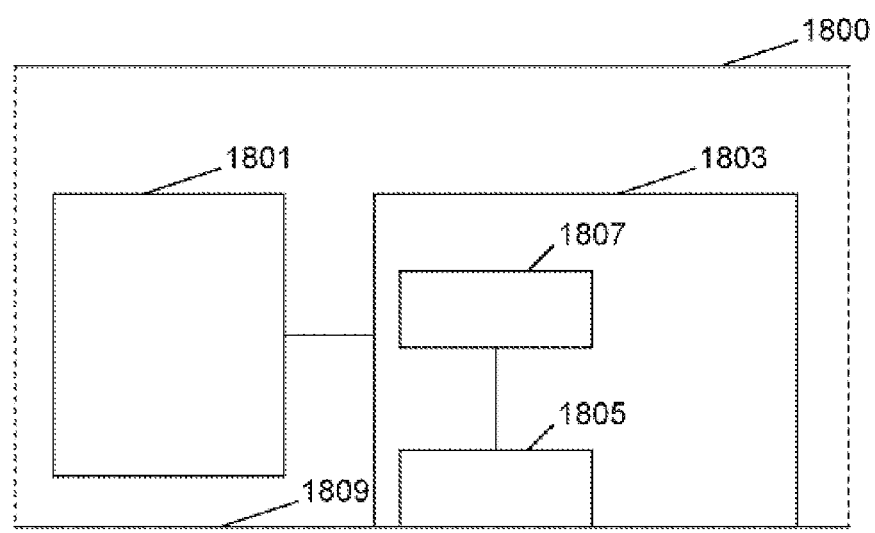
FIG. 18 shows a block diagram of a section of an armband.

FIG. 18 shows a block diagram of a section of an exemplary embodiment of an armband 1800. The armband 1800 has a detection device 1801 and a setting device 1803. The detection device 1801 and the setting device 1803 are embodied at least like the detection device 1701 and the setting device 1703 of FIG. 17. Furthermore, the setting device 1803 of FIG. 18 has a sensor apparatus 1805 and a control apparatus 1807. The sensor apparatus 1805 is configured to measure a current contact pressure of the armband 1800 on the arm. Depending on the measured current contact pressure, the control apparatus 2007 sets the predetermined contact pressure on the arm.

Figure 19:
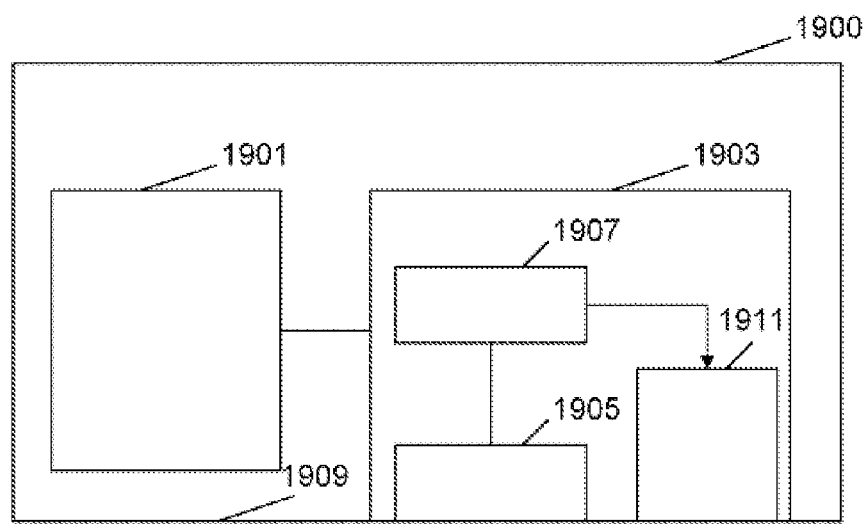
FIG. 19 shows a block diagram of an armband.

FIG. 19 shows a block diagram of a section of a further exemplary embodiment of an armband 1900. The armband 1900 has a detection device 1901 and a setting device 1903. The setting device 1903 has a sensor apparatus 1905, a control apparatus 1907 and an air pump 1911. The sensor apparatus 1905 detects a current contact pressure of the armband 1900 on the arm. The control apparatus 1907 provides a control signal depending on the measured current contact pressure. By means of the provided control signal, the air pump 1911 is controlled for inflating the armband 1900.

Figure 20:
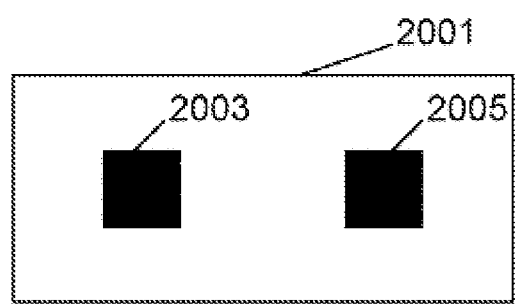
FIG. 20 shows a block diagram of an arrangement of the electrodes of the detection device.

FIG. 20 illustrates a schematic block diagram of an arrangement 2000 of the electrodes, i.e. antennas 2003, 2005 of the detection device for detecting a blood picture parameter of blood in a blood vessel of the arm.

Without loss of generality, the arrangement 2000 only shows two electrodes 2003 and 2005. In particular, the arrangement 2000 is part of the detection device and, for example, embodied as a plate with exemplary dimensions of 5 cm by 2 cm. The electrodes 2003, 2005 for example have a base area of 5 mm by 5 mm. By way of example, the distance between the electrodes 2003, 2005 is 1 to 2 cm. This firstly obtains a strong enough transmission and secondly ensures a sufficiently deep penetration depth into the body.

The invention claimed is:

1. A detection device for detecting a blood picture parameter of blood in a blood vessel, comprising:
    a transmitter, which is configured to couple a first transmission signal with a first frequency and a second transmission signal with a second frequency into the blood vessel;
    a receiver, which is configured to receive a first reception signal at the first frequency based on a reflection of the first transmission signal and a second reception signal at the second frequency based on reflection of the second transmission signal;
    a computer for detecting losses associated with the first and second transmission signals, which is configured to:
    ascertain a first loss variable on the basis of the first transmission signal and the first reception signal at the first frequency, the first loss variable indicating an electromagnetic excitation of blood in the blood vessel at the first frequency; and
    ascertain a second loss variable on the basis of the second transmission signal and the second reception signal at the second frequency, the second loss variable indicating an electromagnetic excitation of blood in the blood vessel at the second frequency;
    analyze loss variables from a plurality of transmitter and receiver detection configurations, and select an optimum detection configurations therefrom;
    a processor, which is configured to:
    ascertain a first frequency shift of the first loss variable relative to a first reference loss variable, the first frequency shift indicating a viscosity of the blood at the first frequency;
    ascertain a second frequency shift of the second loss variable relative to a second reference loss variable, the second frequency shift indicating a viscosity of the blood at the second frequency; and
    ascertain the blood picture parameter on the basis of the first frequency shift and the second frequency shift, the blood picture parameter indicating a concentration of a blood constituent in the blood;
    wherein the transmitter for coupling-in the first transmission signal or the second transmission signal comprises at least one transmission antenna, and wherein the receiver for receiving the first reception signal and the second reception signal comprises at least one reception antenna.

2. The detection device as claimed in claim 1, further comprising a storage medium for providing the first reference loss variable and the second reference loss variable.

3. The detection device as claimed in claim 1, wherein the first loss variable is an absorption line of a water solution with a blood constituent at the first frequency and wherein the second loss variable is an absorption line of the water solution at the second frequency.

4. The detection device as claimed in claim 1, wherein the first loss variable and the second loss variable define a frequency-dependent profile of the absorption of a water solution with a blood constituent and wherein the first reference variable and the second reference variable define a frequency-dependent profile of the absorption of the water solution at a reference concentration of the blood constituent.

5. The detection device as claimed in claim 1, wherein the first loss variable is an absorption minimum or an absorption maximum in a first frequency range comprising the first frequency and wherein the second loss variable is an absorption minimum or an absorption maximum in a second frequency range comprising the second frequency.

6. The detection device as claimed in claim 1, wherein the first frequency and the second frequency respectively lie in a frequency range between 1 GHz and 15 GHz.

7. The detection device as claimed in claim 1, wherein the computer for detecting losses is configured to ascertain the first loss variable and the second loss variable by a two-port measurement.

8. The detection device as claimed in claim 1, wherein the computer for detecting losses comprises a network analyzer or a power detector.

9. The detection device as claimed in claim 1, wherein the computer for detecting losses is configured to ascertain in each case a forward transmission factor $S_{21}$ and an input reflection factor $S_{11}$ to ascertain the first loss variable and the second loss variable.

10. The detection device as claimed in claim 9, wherein the computer for detecting losses is configured to ascertain in each case the first loss variable and the second loss variable on the basis of the following formula:

$$P_{loss} = 1 - |S_{11}|^2 - |S_{21}|^2,$$

where $p_{loss}$ denotes the respective loss variable, and where $S_{11}$ denotes the input reflection factor and $S_{21}$ denotes the forward transmission factor.

11. The detection device as claimed in claim 1, wherein the transmitter is configured to couple the first transmission signal or the second transmission signal into the blood vessel as a mode or a wave type.

12. The detection device as claimed in claim 11, wherein the transmitter is configured to couple the first transmission signal or the second transmission signal into the blood vessel as a transverse electric wave, a transverse magnetic wave, or a transverse electromagnetic wave.

13. The detection device as claimed in claim 11, wherein the transmitter is configured to couple the first transmission signal or the second transmission signal into the blood vessel longitudinally or transversely with respect to a flow of the blood vessel or to a blood flow direction.

14. The detection device as claimed in claim 1, wherein the blood constituent is a sugar, a lactate, lactic acid, or oxygen.

15. The detection device as claimed in claim 14, wherein the blood constituent is glucose.

16. The detection device as claimed in claim 1, wherein the transmission antenna is a dipole antenna or a frame antenna.

17. The detection device as claimed in claim 1, wherein the reception antenna is a dipole antenna, a frame antenna, or a patch antenna.

18. The detection device as claimed in claim 1, wherein the transmitter is configured to couple the first transmission signal and the second transmission signal into the blood vessel successively by a transmission signal generator or tunable oscillator.

19. The detection device as claimed in claim 1, wherein the transmitter is configured to couple the first transmission signal and the second transmission signal into the blood vessel simultaneously by a broadband signal comprising the first transmission signal and the second transmission signal.

20. A method for detecting a blood picture parameter of blood in a blood vessel, comprising the following steps:
    coupling a first transmission signal with a first frequency into the blood vessel, and optimizing the coupling for a mode of electromagnetic excitation within an extent of the blood vessel;
    coupling a second transmission signal with a second frequency into the blood vessel, and optimizing the coupling for a mode of electromagnetic excitation within an extent of the blood vessel;
    receiving a first reception signal at the first frequency;
    receiving a second reception signal at the second frequency;
    establishing, by a computer for detecting losses associated with the first and second transmission signals, a first loss variable on the basis of the first transmission signal and the first reception signal at the first frequency, the first loss variable indicating an electromagnetic excitation of blood in the blood vessel at the first frequency;
    establishing, by the computer for detecting losses associated with the first and second transmission signals, a second loss variable on the basis of the second transmission signal and the second reception signal at the second frequency, the second loss variable indicating an electromagnetic excitation of blood in the blood vessel at the second frequency;
    ascertaining a first frequency shift of the first loss variable relative to a first reference loss variable, the first frequency shift indicating a viscosity of the blood at the first frequency;
    ascertaining a second frequency shift of the second loss variable relative to a second reference loss variable, the second frequency shift indicating a viscosity of the blood at the second frequency; and
    ascertaining the blood picture parameter on the basis of the first frequency shift and of the second frequency shift, the blood picture parameter indicating a concentration of a blood constituent in the blood.

* * * * *